(12) United States Patent
Kim et al.

(10) Patent No.: US 10,687,775 B2
(45) Date of Patent: Jun. 23, 2020

(54) CEPHALOMETRIC X-RAY IMAGE ACQUISITION DEVICE CAPABLE OF ACQUIRING THREE-DIMENSIONAL FACIAL OPTICAL IMAGE AND CEPHALOMETRIC X-RAY IMAGE

(71) Applicants: VATECH Co., Ltd., Gyeonggi-do (KR); VATECH EWOO Holdings Co., Ltd., Gyeonggi-do (KR)

(72) Inventors: Yeong Kyun Kim, Gyeonggi-do (KR); Tae Woo Kim, Gyeonggi-do (KR); Sung Il Choi, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 149 days.

(21) Appl. No.: 15/778,828

(22) PCT Filed: Nov. 24, 2016

(86) PCT No.: PCT/KR2016/013596
§ 371 (c)(1),
(2) Date: May 24, 2018

(87) PCT Pub. No.: WO2017/090994
PCT Pub. Date: Jun. 1, 2017

(65) Prior Publication Data
US 2018/0344278 A1    Dec. 6, 2018

(30) Foreign Application Priority Data

Nov. 24, 2015  (KR) .................... 10-2015-0164938

(51) Int. Cl.
*A61B 6/00*    (2006.01)
*A61B 5/00*    (2006.01)
*G06T 7/30*    (2017.01)
*A61B 6/14*    (2006.01)
*A61B 6/06*    (2006.01)

(52) U.S. Cl.
CPC .......... *A61B 6/5205* (2013.01); *A61B 5/0035* (2013.01); *A61B 5/0064* (2013.01);
(Continued)

(58) Field of Classification Search
CPC ........... A61B 6/06; A61B 6/14; A61B 5/0064; A61B 5/0077; A61B 5/0035;
(Continued)

(56) References Cited

U.S. PATENT DOCUMENTS 6,081,739 A * 6/2000 Lemchen ............. A61B 5/0064
600/407
2004/0264624 A1 * 12/2004 Tanaka ................ A61B 6/0478
378/4

KR 10-2010-0115000/2010
(Continued)

FOREIGN PATENT DOCUMENTS

KR  10-2008-0012053 A   2/2008
KR  10-2008-0104722 A   12/2008
(Continued)

OTHER PUBLICATIONS

Korean Intellectual Property Office, International Search Report of International Application No. PCT/KR2016/013596, dated Feb. 20, 2017.
Korean Intellectual Property Office, Written Opinion of International Application No. PCT/KR2016/013596, dated Feb. 20, 2017.

*Primary Examiner* — Yon J Couso
(74) *Attorney, Agent, or Firm* — IP Legal Services, LLC

(57) ABSTRACT

The present invention relates generally to a cephalometric X-ray image acquisition device. More particularly, the present invention relates to a cephalometric X-ray image acquisition device capable of providing a three-dimensional facial optical image and a cephalometric X-ray image of a subject.

6 Claims, 5 Drawing Sheets

(52) U.S. Cl.
CPC .............. *A61B 5/0077* (2013.01); *A61B 6/44* (2013.01); *A61B 6/501* (2013.01); *G06T 7/30* (2017.01); *A61B 6/06* (2013.01); *A61B 6/14* (2013.01); *G06T 2207/10028* (2013.01); *G06T 2207/10116* (2013.01); *G06T 2207/30201* (2013.01)

(58) Field of Classification Search
CPC ......... A61B 6/5205; A61B 6/501; A61B 6/44; A61B 6/5247; A61B 6/466; G06T 2207/30201; G06T 2207/10028; G06T 7/30; G06T 2207/10116
See application file for complete search history.

(56) References Cited

U.S. PATENT DOCUMENTS

2010/0128840 A1   5/2010  Cha
2012/0243662 A1*  9/2012  Loustauneau ............ A61B 6/06
    378/63
2014/0334599 A1  11/2014  Choi et al.

FOREIGN PATENT DOCUMENTS

KR    10-2011-0006984 A    1/2011
KR    10-2012-0126588 A   11/2012

\* cited by examiner

CEPHALOMETRIC X-RAY IMAGE ACQUISITION DEVICE CAPABLE OF ACQUIRING THREE-DIMENSIONAL FACIAL OPTICAL IMAGE AND CEPHALOMETRIC X-RAY IMAGE

CROSS REFERENCE TO RELATED APPLICATIONS

This application is a National Stage Patent Application of PCT International Patent Application No. PCT/KR2016/013596 (filed on Nov. 24, 2016) under 35 U.S.C. § 371, which claims priority to Korean Patent Application No. 10-2015-0164938 (filed on Nov. 24, 2015), the teachings of which are incorporated herein in their entireties by reference.

TECHNICAL FIELD

The present invention relates generally to a cephalometric X-ray image acquisition device. More particularly, the present invention relates to a cephalometric X-ray image acquisition device capable of providing a three-dimensional facial optical image and a cephalometric X-ray image of a subject.

BACKGROUND ART

A cephalometric X-ray image is a two-dimensional X-ray image of a subject's head.

The cephalometric X-ray image is an important image for dental orthodontic treatment diagnosis of jaw correction surgery because it can show dental and skeletal images for dental orthodontic treatment or diagnosis of jaw correction surgery.

Meanwhile, for dental orthodontic treatment diagnosis of jaw correction surgery, a facial optical image as well as X-ray images of subject's dentition and skeleton is required, the optical image can be imaged using an optical camera.

However, the cephalometric X-ray image and the optical image are all two-dimensional images, so there is a limit to the diagnosis of the skeletal structure of the three-dimensional subject.

Recently, CT (computed tomography) that can diagnose by providing three-dimensional X-ray images of the dentition or skeleton has been developed thanks to the development of medical technology, but CT is problematic in that since it is expensive, and an exposure dose of X-rays is high, the subject is reluctant to undergo CT and may undergo CT imaging only once or twice due to cost burden and an increase in X-ray exposure.

Therefore, two-dimensional images such as a cephalometric X-ray image and a facial optical image are used in diagnosis and treatment evaluation of orthodontic treatment or jaw correction surgery in current dental clinics.

DISCLOSURE

Technical Problem

Accordingly, the present invention has been made keeping in mind the above problems occurring in the related art, and one object of the present invention is to provide a cephalometric X-ray image acquisition device capable of showing X-ray images of subject's dentition and skeleton and a three-dimensional facial optical image simultaneously by acquiring both the cephalometric X-ray image and the three-dimensional facial optical image, and allowing the subject head to be interpreted three-dimensionally.

The objects of the present invention are not limited to the above-mentioned objects, and other objects not mentioned can be clearly understood by those skilled in the art from the following description.

Technical Solution

In order to achieve the above object, according to some aspects of the present invention, there is provided a cephalometric X-ray image acquisition device including: an X-ray source configured to irradiate X-rays toward a subject's head; a cephalometric sensor disposed to face the X-ray source with the subject's head therebetween, and configured to receive the X-rays transmitted through the subject's head to acquire a cephalometric X-ray image of the subject; and a three-dimensional camera configured to acquire a three-dimensional facial optical image with depth information by imaging a face of the subject while moving around the subject's head.

In a preferred embodiment, the cephalometric X-ray image acquisition device further includes a sensor support configured to support the cephalometric sensor.

In a preferred embodiment, the cephalometric X-ray image acquisition device further includes a camera mount arm configured such that a first end thereof is movably connected to the sensor support and the three-dimensional camera is mounted to a second end thereof, wherein the three-dimensional camera moves around the subject's head along the camera mount arm.

In a preferred embodiment, the cephalometric X-ray image acquisition device further includes at least one light source provided in the camera mount arm and moved along with the three-dimensional camera, and configured to emit light toward the subject's head.

In a preferred embodiment, the cephalometric X-ray image acquisition device further includes a collimator provided in the sensor support between the X-ray source and the cephalometric sensor, with the three-dimensional camera mounted thereto, wherein the three-dimensional camera moves around the subject's head along the collimator.

In a preferred embodiment, the cephalometric X-ray image acquisition device further includes at least one light source provided in the collimator and moved along with the three-dimensional camera, and configured to emit light toward the subject's head.

In a preferred embodiment, the cephalometric X-ray image acquisition device further includes an image processor configured to receive the cephalometric X-ray image and the three-dimensional facial optical image, and align the cephalometric X-ray image with the three-dimensional facial optical image.

Advantageous Effects

The present invention has the following advantages.

According to the cephalometric X-ray image acquisition device of the present invention, a cephalometric X-ray image and a three-dimensional facial optical image are acquired and are aligned with each other, whereby it is possible to show images of dentition, the skeleton, and face of a subject simultaneously, and it is possible for a doctor to interpret the subject head three-dimensionally.

Figure 1:
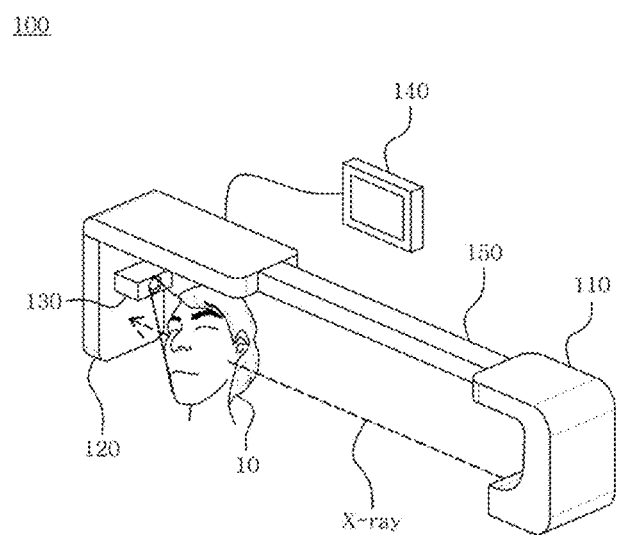
FIG. 1 is a view showing a cephalometric X-ray image acquisition device according to a first embodiment of the present invention.

DESCRIPTION OF REFERENCE CHARACTERS OF IMPORTANT PARTS 100, 200, 300: cephalometric X-ray image acquisition device
110: X-ray source 120: cephalometric sensor
130: three-dimensional camera 140: image processor
150: support arm 210: collimator
310: camera mount arm

BEST MODE

Unless otherwise defined, all terms including technical and scientific terms used herein have the same meaning as commonly understood by one of ordinary skill in the art to which the present invention belongs. It will be further understood that terms used herein should be interpreted as having a meaning that is consistent with their meaning in the context of this specification.

Hereinafter, elements of the present invention will be described in detail with reference to preferred embodiments shown in the accompanying drawings.

The present invention is not limited to the embodiments described herein but may be embodied in other forms. Throughout the drawings and the description, the same reference numerals will be used to refer to the same or like elements or parts.

Referring to FIG. 1, a cephalometric X-ray image acquisition device 100 according to an embodiment of the present invention includes an X-ray source 110, a cephalometric sensor 120, and a three-dimensional camera 130.

Further, although not shown, between the X-ray source 110 and the cephalometric sensor 120, a CT/panoramic sensor may be provided to image CT (computed tomography) image or panoramic image.

The X-ray source 110 generates X-rays and irradiates the generated X-rays toward a subject's head 10.

Further, the X-ray source 110 may be any of various known X-ray sources such as cold-cathode X-ray tube or hot-cathode X-ray tube.

Further, when the X-ray source 110 is equipped with a small cold-cathode X-ray tube using the field emission effect of a nanostructure material such as a carbon nanotube, a plurality of X-ray tubes may constitute one X-ray source.

The cephalometric sensor 120 is an X-ray sensor that is disposed to face the X-ray source 110 with the subject's head 10 therebetween and is configured to receive the X-rays transmitted through the subject's head 10 to acquire a cephalometric X-ray image of the subject.

Further, the cephalometric sensor 120 may be a so-called one-shot type cephalometric sensor that is formed in a large-sized quadrangular shape and acquires the cephalometric X-ray image at a time while the position is fixed, or may be a so-called scan type cephalometric sensor that is formed in a small-sized slit shape and acquires the cephalometric X-ray image in a scanning manner by moving a predetermined distance around the subject's head.

Further, the cephalometric sensor 120 and the X-ray source 110 are connected via a support arm 150 so that the relative position can be adjusted and determined.

The three-dimensional camera 130 is disposed to face the subject's head 10, and acquires a three-dimensional facial optical image that is three-dimensional optical image with depth information.

Further, the three-dimensional camera 130 is attached to the cephalometric sensor 120.

However, the three-dimensional camera 130 may be attached to the X-ray source 110 or the support arm 150 as long as it faces the subject's head 10.

Further, the three-dimensional camera 130 can acquire the three-dimensional facial optical image through confocal microscopy, stereo vision, active stereo vision, active triangulation, active wavefront sampling, accordion fringe interferometry, or optical coherence tomography. Here, if necessary, the three-dimensional camera 130 may include a pattern projector that projects a predetermined pattern toward the subject, and may further include a digital camera for acquiring a color image of the subject.

In other words, according to the cephalometric X-ray image acquisition device 100 of a first embodiment of the present invention, it is possible to provide a three-dimensional facial optical image instead of a simple two-dimensional optical image, thereby enabling a doctor to effectively perform diagnosis and treatment evaluation of orthodontic treatment or jaw correction surgery.

Further, the cephalometric X-ray image acquisition device 100 according to the first embodiment of the present invention may further include an image processor 140 configured to receive the cephalometric X-ray image and the three-dimensional facial optical image, and align the cephalometric X-ray image with the three-dimensional facial optical image.

Figure 2:
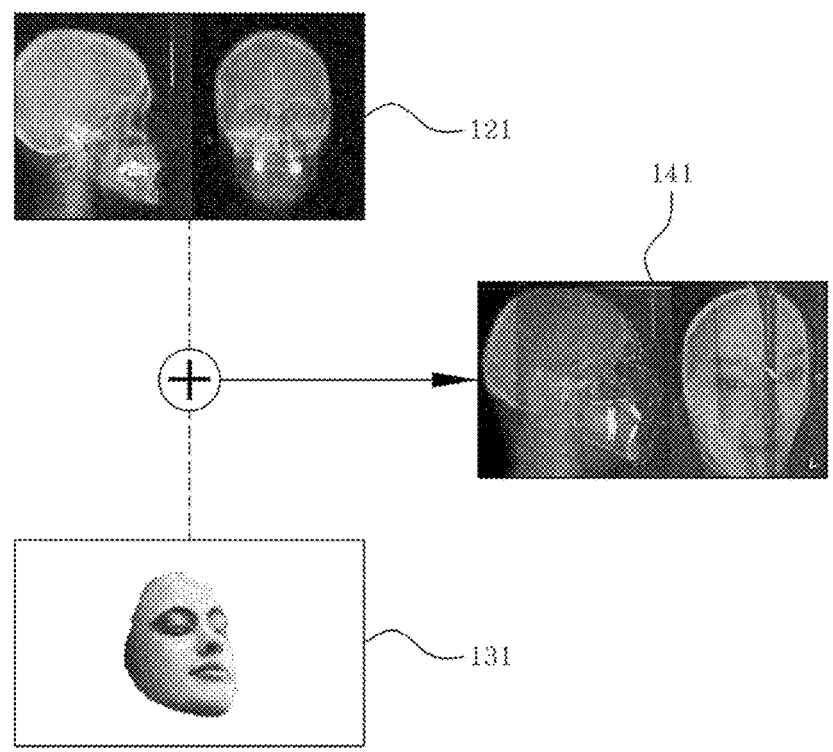
FIG. 2 is a view showing a cephalometric X-ray image acquired by the cephalometric X-ray image acquisition device according to embodiments of the present invention.

To be more specific, with reference to FIG. 2, the image processor 140, firstly, receives both a cephalometric X-ray image 121 including at least one of a posteroanterior face and a lateral face of the subject from the cephalometric sensor 120 and a three-dimensional facial optical image 131 with depth information from the three-dimensional camera 130, and then aligns the cephalometric X-ray image 121 and the three-dimensional facial optical image 131 with each other, thereby acquiring a cephalometric X-ray image 141 aligned with a three-dimensional facial optical image. When aligning the cephalometric X-ray image 121 with the three-dimensional facial optical image 131, the positions of the cephalometric sensor 120 and the three-dimensional camera 130 may be referred to.

Further, the cephalometric X-ray image 141 aligned with a three-dimensional facial optical image may be provided by being reconstructed in the front, side, or diagonal direction of the subject, and may be provided as a three-dimensional image so that a doctor can rotate the image on the computer.

In other words, according to the cephalometric X-ray image acquisition device 100 of the first embodiment of the present invention, the subject's dentition, skeleton, and three-dimensional facial optical image can be superimposed on each other, so it can be effectively used for diagnosis and treatment of the subject.

MODE FOR INVENTION

Second Embodiment

Figure 3:
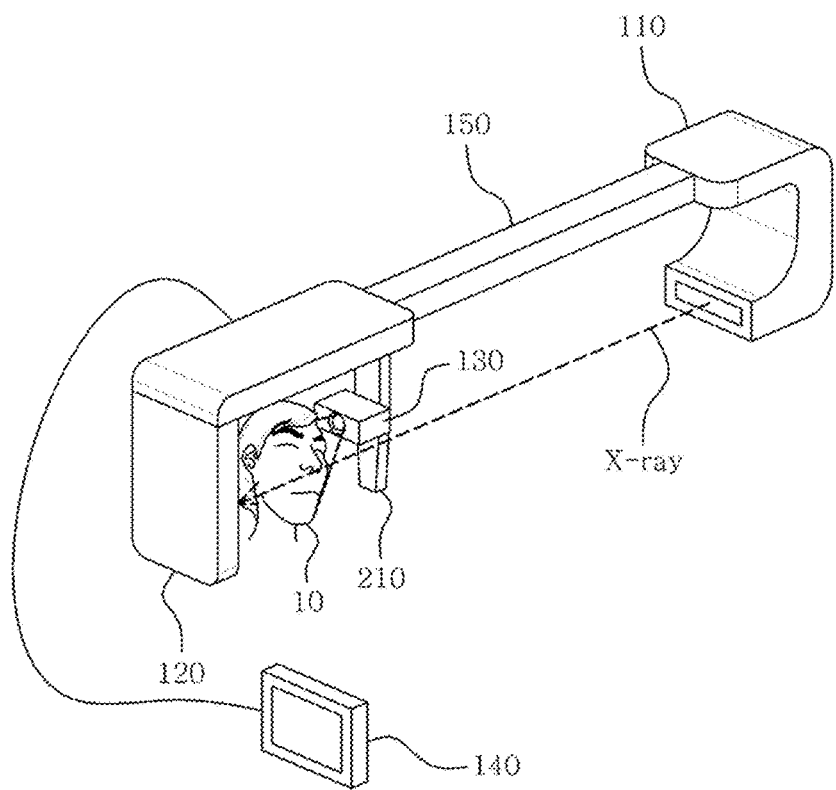
FIG. 3 is a view showing a cephalometric X-ray image acquisition device according to a second embodiment of the present invention.

FIG. 3 is a view showing a cephalometric X-ray image acquisition device according to a second embodiment of the present invention, wherein a cephalometric X-ray image acquisition device 200 according to the second embodiment of the present invention includes an X-ray source 110, a cephalometric sensor 120, a three-dimensional camera 130, an image processor 140, and a collimator 210.

Further, the cephalometric X-ray image acquisition device 200 according to the second embodiment of the present invention further includes the collimator 210 in addition to the X-ray source 110, the cephalometric sensor 120, the three-dimensional camera 130, and the image processor 140 in comparison to the cephalometric X-ray image acquisition device 100 according to the first embodiment of the present invention.

Here, the cephalometric X-ray image acquisition device 200 according to the second embodiment of the present invention may include a sensor support (see reference numeral 151 in FIG. 5, hereinafter the same) configured to support the cephalometric sensor 120 and the collimator 210 with the subject therebetween, wherein the collimator 210 is provided in the sensor support 131 between the X-ray source 110 and the cephalometric sensor 120 and adjusts an irradiation field of X-rays scanning the subject's head 10 while moving along the subject's head during a so-called scan-type cephalometric X-ray imaging.

Further, the collimator 210 is made of a radiation-absorbing material such as lead or tungsten to limit the direction and diffusion of X-rays, and is also referred to as a second collimator to distinguish it from a first collimator that is often embedded in the X-ray source 110.

Further, the three-dimensional camera 130 is attached to the collimator 210.

In other words, in comparison to the cephalometric X-ray image acquisition device 100 according to the first embodiment of the present invention, the cephalometric X-ray image acquisition device 200 according to the second embodiment of the present invention is different in that the three-dimensional camera 130 is provided in the collimator 210 to perform three-dimensional facial optical imaging.

Further, although not shown, the collimator 210 may be provided with a light source capable of irradiating light toward the subject, wherein the light source performs a lighting function so as to obtain a clear image by emitting light toward the subject when the three-dimensional camera 130 performs imaging of the subject.

Further, the light source may be constituted by one or multiple LEDs.

Third Embodiment

Figure 4:
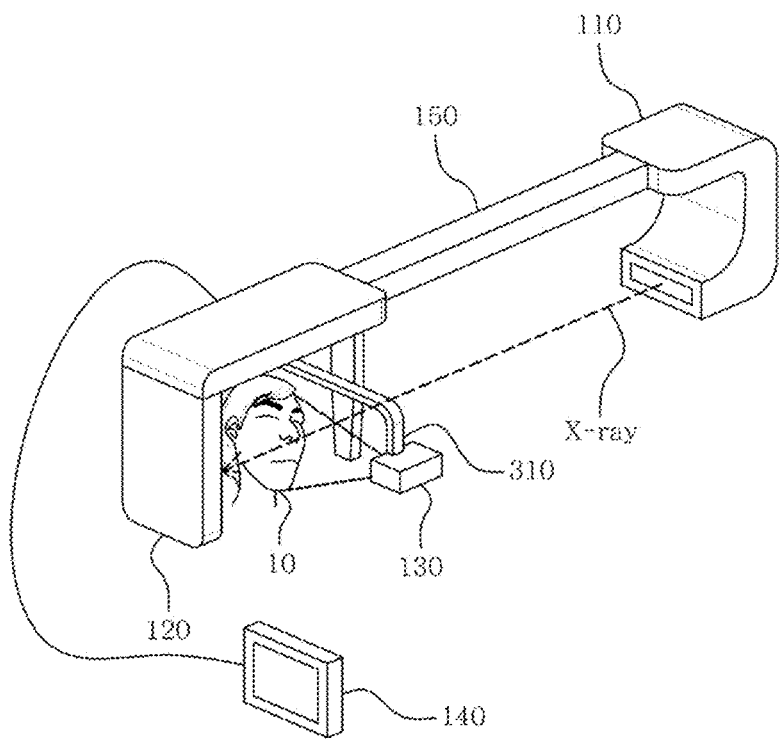
FIG. 4 is a view showing a cephalometric X-ray image acquisition device according to a third embodiment of the present invention.

FIG. 4 is a view showing a cephalometric X-ray image acquisition device according to a third embodiment of the present invention, wherein a cephalometric X-ray image acquisition device 300 according to the third embodiment of the present invention includes an X-ray source 110, a cephalometric sensor 120, a three-dimensional camera 130, an image processor 140, and a camera mount arm 310.

Further, the cephalometric X-ray image acquisition device 300 according to the third embodiment of the present invention further includes the camera mount arm 310 in addition to the X-ray source 110, the cephalometric sensor 120, the three-dimensional camera 130, and the image processor 140 in comparison to the cephalometric X-ray image acquisition device 100 according to the first embodiment of the present invention.

Further, the cephalometric X-ray image acquisition device 300 according to the third embodiment of the present invention may further include a collimator 210 that is provided in the cephalometric X-ray image acquisition device 200 according to the second embodiment of the present invention.

The camera mount arm 310 is a means that positions and moves the three-dimensional camera 130 to face the subject's face, and may be attached to the support arm 150.

However, the camera mount arm 310 has no particular restriction on the attachment position, as long as it can position and move the three-dimensional camera 130 to face the subject's face.

Further, the camera mount arm 310 can control the direction and position wherein the three-dimensional camera 130 faces the subject's face while linearly moving or rotating on the support arm 150, and the three-dimensional camera 130 can move in a predetermined direction on the camera mount arm 310.

Figure 5:
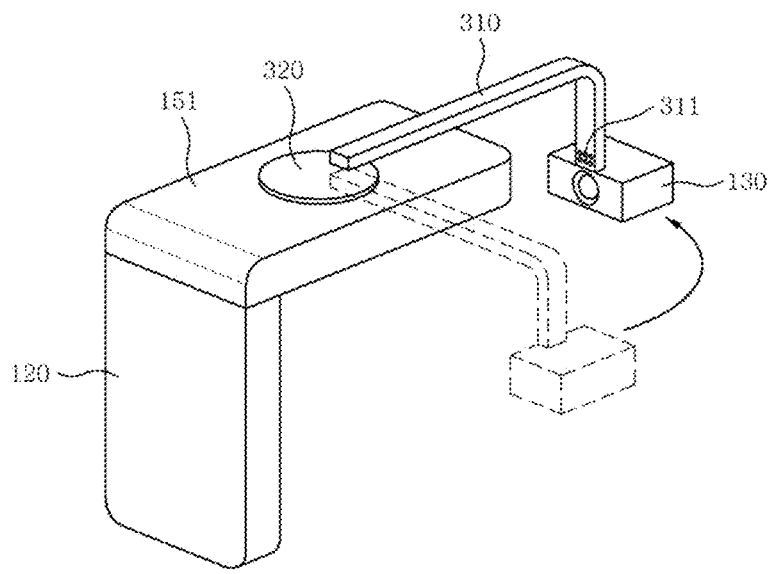
FIG. 5 is a view showing an example of combining a camera mount arm of the cephalometric X-ray image acquisition device according to the third embodiment of the present invention.

Further, FIG. 5 is a view showing an example where the camera mount arm 310 is connected to the support arm 150, wherein referring to FIG. 5, the camera mount arm 310 is rotatably connected to a sensor support 151 for supporting the cephalometric sensor 120, as a part of the support arm 150.

To be more specific, the sensor support 151 may be provided with a rotating disk 320 on an upper surface thereof, and the camera mount arm 310 may be attached to the rotating disk 320 or may be coupled to a guide rail to be rotatable on the sensor support 151.

Further, the rotating disk 320 may be provided on a lower surface of the sensor support 151, and in this case, the three-dimensional camera 130 may be connected directly to the rotating disk 320, and the camera mount arm 310 may be omitted. For reference, the sensor support 151 includes a motor and a gear to rotate the rotating disk 320.

Further, the camera mount arm 310 may be provided with a light source 311 capable of irradiating light toward a subject at a position facing the subject, wherein the light source 311 performs a lighting function so as to obtain a clear image by emitting light when the three-dimensional camera 130 performs imaging of the subject.

Further, the light source 311 may be constituted by one or multiple LEDs.

FIGS. 6 to 9 are schematic top views of the subject's head 10 to illustrate how the cephalometric sensor 120 and the three-dimensional camera 130 perform imaging, respectively.

Figure 6:
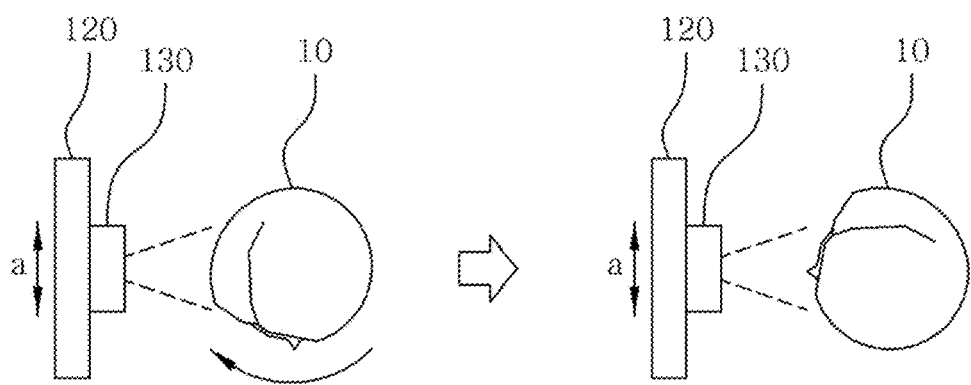
FIGS. 6 to 9 are views showing operation of the cephalometric X-ray image acquisition device according to embodiments of the present invention.

Firstly, FIG. 6 shows a case where the three-dimensional camera 130 is provided in the cephalometric sensor 120.

In this case, the cephalometric sensor 120 and the three-dimensional camera 130 are fixed to face the subject's head 10, and the subject changes his or her posture such that the front and side of head 10 are imaged.

Herein, when the cephalometric sensor 120 is a scan-type cephalometric sensor, the cephalometric sensor 120 can obtain the cephalometric X-ray image while moving in an 'a' axis direction, and the three-dimensional camera 130 can obtain the three-dimensional facial optical image while also moving in the 'a' axis direction along with the cephalometric sensor 120.

Figure 7:
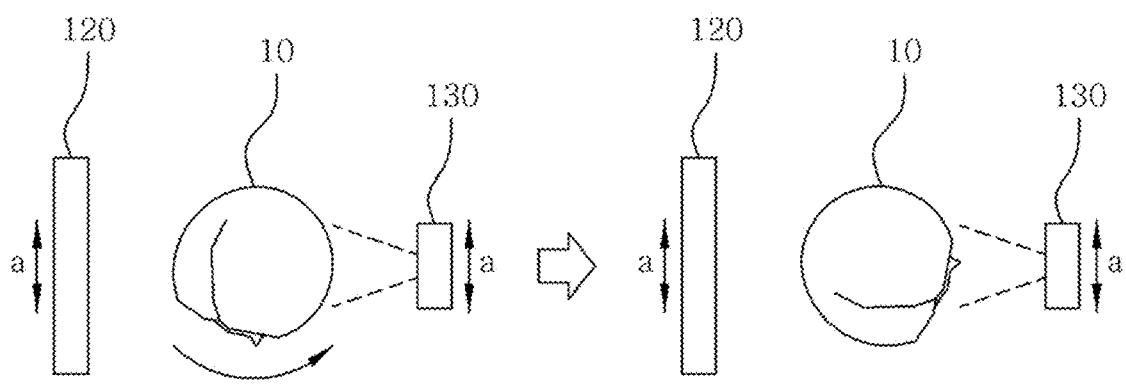

Next, FIG. 7 shows a case where the three-dimensional camera 130 is provide in the X-ray source 110 or the collimator 210.

Also in this case, the cephalometric sensor 120 and the three-dimensional camera 130 are fixed to face the subject's head 10, and the subject changes his or her posture such that the front and side of head 10 are imaged.

Herein, when the cephalometric sensor 120 is a scan-type cephalometric sensor, the cephalometric sensor 120 can obtain the cephalometric X-ray image while moving in an 'a' axis direction, and the three-dimensional camera 130 can obtain the three-dimensional facial optical image while moving in the 'a' axis direction on the X-ray source 110 or on the collimator 210.

Here, the collimator 210 may move in the 'a' axis direction, and in this case, the three-dimensional camera 130 may be fixed in the collimator 210.

Figure 8:
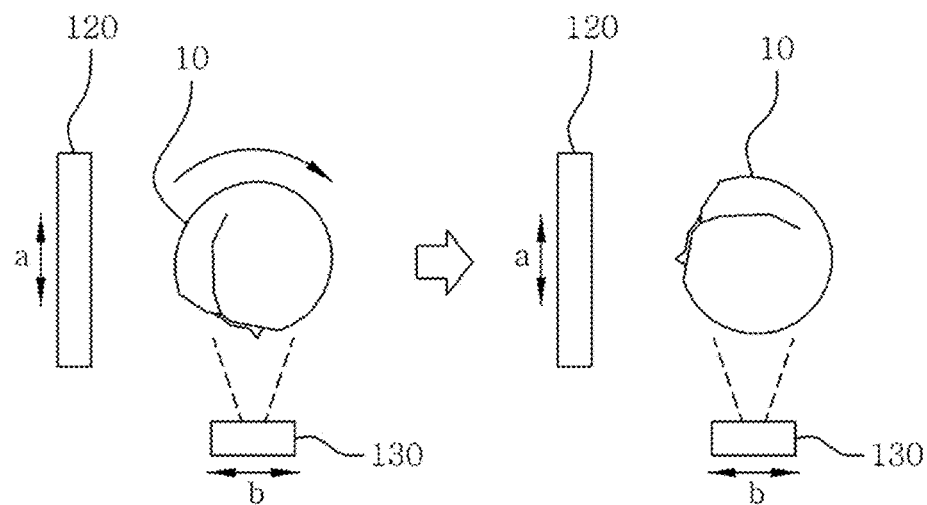
Figure 9:
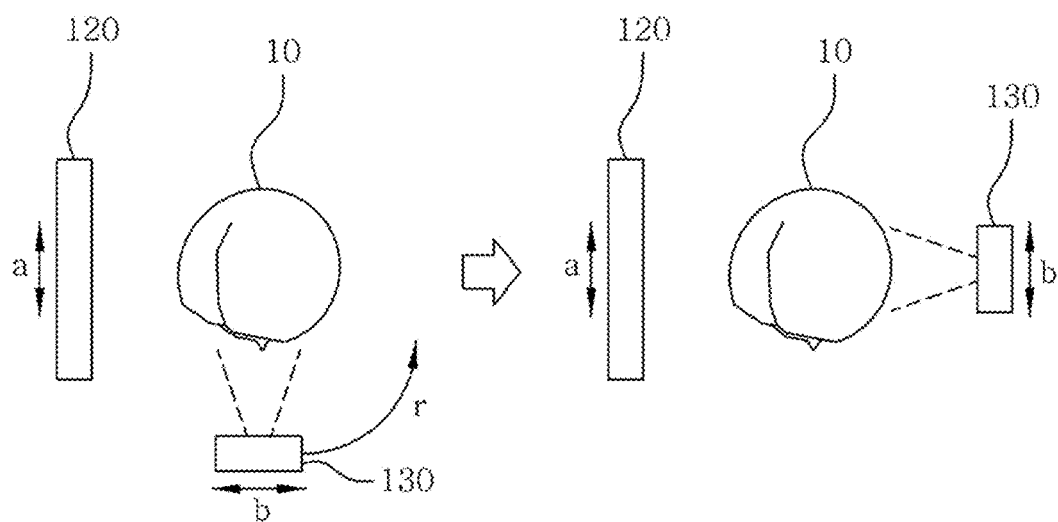

Next, FIGS. 8 and 9 show a case where the three-dimensional camera 130 is mounted to the camera mount arm 310, wherein FIG. 8 shows a case where the cephalometric sensor 120 and the camera 130 are fixed, and in this case, the subject changes his or her posture such that the front and side of the subject's head 10 are imaged.

Herein, when the cephalometric sensor 120 is a scan-type cephalometric sensor, the cephalometric sensor 120 can obtain the cephalometric X-ray image while moving in an 'a' axis direction, and the three-dimensional camera 130 can obtain the three-dimensional facial optical image while moving in a 'b' axis direction different from the 'a' axis direction on the camera mount arm 310.

Further, FIG. 9 shows a case where the camera mount arm 310 is mounted to the rotatable camera mount arm 310, wherein the three-dimensional camera 130 can obtain the three-dimensional facial optical image while rotating about the subject's head 10 by the camera mount arm 310.

Further, also in this case, the cephalometric sensor 120, which is a scan-type cephalometric sensor, can obtain the cephalometric X-ray image while moving in the 'a' axis direction, and the three-dimensional camera 130 can obtain the three-dimensional facial optical image while moving in the 'b' axis direction on the camera mount arm 310.

Although a preferred embodiment of the present invention has been described for illustrative purposes, those skilled in the art will appreciate that various modifications, additions and substitutions are possible, without departing from the scope and spirit of the invention as disclosed in the accompanying claims.

INDUSTRIAL APPLICABILITY

The cephalometric X-ray image acquisition device of the present invention can provide a medical cephalometric X-ray image aligned with a three-dimensional facial optical image of a subject.

The invention claimed is:

1. A cephalometric X-ray image acquisition device comprising:
   an X-ray source configured to irradiate X-rays toward a subject's head;
   a cephalometric sensor disposed to face the X-ray source with the subject's head therebetween, and configured to receive the X-rays transmitted through the subject's head to acquire a cephalometric X-ray image of the subject;
   a three-dimensional camera configured to acquire a three-dimensional facial optical image with depth information by imaging a face of the subject;
   a sensor support configured to support the cephalometric sensor; and
   a camera mount arm configured such that a first end thereof is movably connected to the sensor support and the three-dimensional camera is mounted to a second end thereof,
   wherein the cephalometric sensor obtains the cephalometric X-ray image while moving in a first direction along the sensor supports, the three-dimensional camera obtains the three-dimensional facial optical image while moving in a second direction different from the first direction along the camera mount arm.

2. The cephalometric X-ray image acquisition device of claim 1, further comprising:
   a rotating disk for connecting the camera mount arm to the sensor supports.

3. The cephalometric X-ray image acquisition device of claim 2,
   wherein the sensor support includes a motor and a gear to rotate the rotating disk.

4. The cephalometric X-ray image acquisition device of claim 1, further comprising:
   at least one light source provided in the camera mount arm and moved along with the three-dimensional camera, and configured to emit light toward the subject's head.

5. The cephalometric X-ray image acquisition device of claim 1, further comprising:
   an image processor configured to receive the cephalometric X-ray image and the three-dimensional facial optical image, and align the cephalometric X-ray image with the three-dimensional facial optical image.

6. A cephalometric X-ray image acquisition device comprising:
   an X-ray source configured to irradiate X-rays toward a subject's head;
   a cephalometric sensor disposed to face the X-ray source with the subject's head therebetween, and configured to receive the X-rays transmitted through the subject's head to acquire a cephalometric X-ray image of the subject;
   a three-dimensional camera configured to acquire a three-dimensional facial optical image with depth information by imaging a faced of the subject;
   a sensor support configured to support the cephalometric sensor;
   a camera mount arm configured such that a first end thereof is movably connected to the sensor support and the three-dimensional camera is mounted to a second end thereof,
   wherein the cephalometric sensor obtains the cephalometric X-ray image at a fixed position in the sensor support, the three-dimensional camera obtains the three-dimensional facial optical image by moving along the camera mount arm separately from the sensor.

* * * * *